United States Patent
Mitchell et al.

(10) Patent No.: US 10,376,675 B2
(45) Date of Patent: Aug. 13, 2019

(54) RAPID INSERTION INTEGRATED CATHETER AND METHOD OF USING AN INTEGRATED CATHETER

(71) Applicants: James D. Mitchell, Walnut Creek, CA (US); Andrew A. Thoreson, Vacaville, CA (US)

(72) Inventors: James D. Mitchell, Walnut Creek, CA (US); Andrew A. Thoreson, Vacaville, CA (US)

(73) Assignee: REDSMITH, INC., Walnut Creek, CA (US)

(*) Notice: Subject to any disclaimer, the term of this patent is extended or adjusted under 35 U.S.C. 154(b) by 178 days.

(21) Appl. No.: 15/008,628

(22) Filed: Jan. 28, 2016

(65) Prior Publication Data
US 2016/0220786 A1 Aug. 4, 2016

Related U.S. Application Data (60) Provisional application No. 62/109,403, filed on Jan. 29, 2015.

(51) Int. Cl.
  *A61M 25/06* (2006.01)
  *A61M 25/00* (2006.01)
  *A61M 25/01* (2006.01)

(52) U.S. Cl.
  CPC .... *A61M 25/0606* (2013.01); *A61M 25/0029* (2013.01); *A61M 25/007* (2013.01); *A61M 25/0102* (2013.01); *A61M 2025/0037* (2013.01)

(58) Field of Classification Search
  CPC .......... A61M 25/0606; A61M 25/0029; A61M 25/007; A61M 25/0102; A61M 25/0037; A61M 2025/0063; A61M 25/06; A61M 25/065; A61M 2025/018; A61B 17/3415; A61B 17/3417
  See application file for complete search history.

(56) References Cited

U.S. PATENT DOCUMENTS

| | | | |
|---|---|---|---|
| 3,225,762 A | | 12/1965 | Guttman |
| 4,468,224 A | * | 8/1984 | Enzmann ............. A61M 25/06 604/168.01 |

(Continued)

OTHER PUBLICATIONS

Definition of needle (Merriam-Webster Oct. 16, 2017).*
Definition of channel (Merriam-Webster May 14, 2018).*

*Primary Examiner* — Laura A Bouchelle
*Assistant Examiner* — Dung T Ulsh
(74) *Attorney, Agent, or Firm* — Fisher Broyles LLP; Victoria Brewster; Rachel H. Huffstetler (57) ABSTRACT

An integrated catheter assembly for rapid vascular insertion including a catheter configured for receipt of a needle and a guidewire; a catheter assembly comprising an integrated assembly comprising a catheter, needle, and guidewire; and a method of rapidly inserting a catheter to obtain vascular access. The catheter includes a central lumen for receiving the needle and guidewire. The lumen includes a distal port and a transverse side port adjacent an intermediate portion thereof which provide open vascular communication from two ports between the central lumen and the vasculature. The needle and guidewire, when integrated with the catheter, extend through the transverse side port wherein a proximal end of the needle extends contiguous to and exterior of a proximal portion of the catheter.

18 Claims, 6 Drawing Sheets

(56) References Cited

U.S. PATENT DOCUMENTS

| | | | |
|---|---|---|---|
| 4,525,157 A | 6/1985 | Vaillancourt | |
| 5,040,548 A | 8/1991 | Yock | |
| 5,112,312 A * | 5/1992 | Luther | A61M 25/0637 128/DIG. 26 |
| 5,120,317 A * | 6/1992 | Luther | A61M 25/0631 604/158 |
| 5,295,970 A | 3/1994 | Clinton et al. | |
| 5,306,247 A * | 4/1994 | Pfenninger | A61M 29/02 604/102.02 |
| 5,378,230 A | 1/1995 | Mahurkar | |
| 5,380,290 A | 1/1995 | Makower | |
| 5,573,520 A | 11/1996 | Schwartz et al. | |
| 5,718,678 A | 2/1998 | Fleming, III | |
| 5,947,940 A | 9/1999 | Beisel | |
| 7,029,467 B2 | 4/2006 | Currier et al. | |
| 7,311,697 B2 | 12/2007 | Osborne | |
| 7,938,820 B2 * | 5/2011 | Webster | A61B 17/22 604/528 |
| 8,882,713 B1 * | 11/2014 | Call | A61M 25/09 604/164.01 |
| 2003/0088212 A1 | 5/2003 | Tal | |
| 2003/0100849 A1 * | 5/2003 | Jang | A61M 25/0023 600/585 |
| 2005/0004554 A1 * | 1/2005 | Osborne | A61M 25/0068 604/524 |
| 2005/0245882 A1 | 11/2005 | Elkins et al. | |
| 2008/0125748 A1 * | 5/2008 | Patel | A61M 25/0084 604/509 |
| 2008/0312578 A1 * | 12/2008 | DeFonzo | A61M 25/003 604/6.16 |
| 2012/0157854 A1 | 6/2012 | Kurrus et al. | |
| 2013/0053826 A1 * | 2/2013 | Shevgoor | A61M 25/0015 604/523 |
| 2013/0158338 A1 * | 6/2013 | Kelly | A61M 25/0026 600/16 |
| 2013/0188291 A1 * | 7/2013 | Vardiman | A61N 1/0534 361/117 |
| 2014/0214005 A1 | 7/2014 | Belson | |
| 2014/0276599 A1 * | 9/2014 | Cully | A61M 25/0045 604/507 |
| 2015/0148595 A1 | 5/2015 | Bagwell et al. | |

* cited by examiner

RAPID INSERTION INTEGRATED CATHETER AND METHOD OF USING AN INTEGRATED CATHETER

CROSS-REFERENCE TO RELATED APPLICATION

This application is a continuation of U.S. Provisional Patent Application Ser. No. 62/109,403 filed Jan. 29, 2015, the disclosure of which is hereby incorporated by reference.

FIELD OF THE INVENTION

The present invention is directed to a venous catheter and the method of using the venous catheter, generally, and, more specifically, to a venous catheter assembly with a catheter configured for receipt of an integrated needle and guidewire for rapid insertion and the method of using the integrated catheter.

BACKGROUND OF THE INVENTION

Venous catheters, including central, peripheral, and so-called "midline" or extended-dwell peripheral venous catheters, are used in the medical environment to provide intravenous vascular access. Vascular access by venous catheters provides an expedient and highly effective means for drug administration, other fluid administration, chemotherapy, blood sampling, blood pressure monitoring, and parenteral nutrition, for example. These procedures often require that the catheter be left indwelling in the patient for an extended period of time. In a hospital setting, venous catheters are widely used in emergency departments, intensive care units, and operating rooms. In such settings, it is imperative that the venous catheters be very quickly and correctly positioned intravenously within the patient to obtain vascular access particularly in critical situations requiring rapid administration of medicines.

Highly effective and commonly used venous catheters are triple lumen catheters which are intravenously positioned within any venous structure, including the internal/external jugular, subclavian, or, femoral vein. Triple lumen catheters commonly include a central lumen which extends from the proximal end adjacent the user to the distal end which is positioned within the venous system. Two additional lumens may extend from the proximal end and terminate at a location adjacent to, but proximally removed from, the distal end of the catheter and terminate in open side ports. U.S. Pat. No. 7,311,697 B2 is an exemplary triple lumen catheter.

A widely accepted and commonly used percutaneous entry technique used to obtain access to the venous system of a patient requiring a venous catheter is a landmark guided technique known as the Seldinger technique. The Seldinger technique involves multiple steps which must be employed in medical conditions necessitating expedient placement of a line, such as in an emergency setting. In the Seldinger technique, the physician makes an oblique entry with a hollow needle through the patients skin, at a peripheral location using landmark guidance, and into a vein. The commonly used Seldinger technique is most often employed in combination with imaging guidance (e.g., ultrasound). Landmark guidance techniques involve visually or palpably locating anatomical landmarks for locating the targeted vein. For example, for subclavian vein entry, the landmark guided technique includes locating the junction of the middle and proximal third of the clavicle and inserting the needle at that location.

A blunt guidewire is then passed through the central lumen of the needle, and then the needle is withdrawn and removed leaving the guidewire within the vein. Next, a dilating device is passed over the guidewire to slightly enlarge the tract originally produced by the needle and, if warranted, multiple dilators having varying gauge, may be utilized, in a process called serial dilation. The dilator is then removed, leaving the guidewire within the vein. The catheter is then passed along the length and over the guidewire until positioned within the vein. Alternatively, use of a peel-away sheath may be used for placement of a catheter. The sheath may be utilized in conjunction with a dilator (also known as an introducer in this setting) for over-the-wire placement into the desired vessel. Once the sheath is within the vessel, the inner dilator (introducer) and wire are removed, allowing for placement of the catheter through the sheath's lumen. The sheath is then removed in a peel-away fashion, leaving only the catheter behind in the vessel. Blood may then be withdrawn from a catheter port to confirm the catheter placement within the vein. The guidewire is then removed from the vein.

With regard to initial percutaneous placement of the catheter, it is important to quickly position the venous catheter within the appropriate vein. This is imperative not only for the comfort of the patient, but also to achieve successful medical outcomes. Risks associated with incorrect catheter placement and multiple attempts at placement of the catheter include an increased risk of catheter related blood-stream infections from loss of sterility. In extreme instances, improper catheter placement may be injurious to adjacent structures such as the carotid artery, with serious consequences such as hemorrhage, stroke, or pseudo aneurysm formation. It is, thus, recognized that catheter placement may be assisted by utilizing real-time ultrasound imaging techniques in order to minimize such complications. Additionally, high quality, portable ultrasound units have become more regularly available to physicians, thereby further facilitating the use of ultrasound assisted venous catheter placement. An exemplary method employing ultrasound guided central venous catheter placement is U.S. Publication. No. WO 2014006403 A1. More recently, vascular access devices have expanded to include midline catheters, or extended dwell peripheral intravenous lines. Midline catheters are longer and more durable than traditional peripheral intravenous catheters. Different than central catheters, midline catheters do not terminate in the vena cava or right atrium. However, they are typically placed in the larger veins of the upper extremity such as the radial, cephalic, median, brachial or basilicvein. Owing to their durability and location, midline catheters can remain in place longer than the traditional 2-3 days for a peripheral intravenous catheter without the same risks of infiltration and infection. Additionally, because of their size and insertion location, midline catheters are inserted using a combination needle puncture and over-the-wire access and insertion procedure. Although this differs somewhat from the Seldinger technique used for central catheters, it lends itself to benefit from the design and procedure described herein.

SUMMARY OF THE INVENTION

The present invention overcomes shortcomings of the prior art by providing a catheter assembly having a catheter configured for receipt of a needle and guidewire along an outer side surface for rapid insertion of the catheter assembly. Preferably, the venous placement of the catheter is facilitated with ultrasound guided techniques. The integrated catheter, that is, a catheter configured for receipt of a needle and guidewire which, according to one aspect, may be pre-assembled, includes at least a lumen for receipt of a transversely inserted needle which extends axially along the length of a distal portion of the lumen. The lumen extends from the proximal to the distal end of the catheter. Preferably one or more additional lumens, or "non-needle" lumens, are provided and extend from the catheter proximal end and terminate at side ports adjacent the catheter distal end. An additional side port, positioned proximal to the one or more non-needle side ports, is also provided on the catheter body and provides a port for receipt of the needle from an outer side surface of the catheter body, substantially in a transverse direction. The needle receiving side port defines the terminal end of a transverse channel which provides an open channel from the needle receiving side port to the needle lumen. According to another aspect of the present invention, the catheter may, therefore, be pre-assembled so as to include the needle and guidewire wherein the needle and the guidewire extend adjacent to and exterior of a proximal side portion of the catheter.

The method of using the catheter assembly according to the present invention includes the steps of pre-assembling the needle and guidewire within the catheter's needle side port to form an integrated catheter assembly; inserting the needle into the patient's venous system, preferably using ultrasound guidance; introducing the guidewire distally along the length of the needle and into the vessel; removing the needle; advancing the catheter distally along the length of the guidewire until positioned within the venous system; removing the guidewire; and confirming proper placement of the catheter. It is also within the scope of the presently described method to advance or remove the needle and guidewire together in the same method step as opposed to independently removing each. Accordingly, the present invention obviates several method steps of the prior Seldinger technique. Specifically, the catheter assembly according to preferred embodiments, utilizes ultrasound guidance to prevent inaccurate catheter placement. Medical complications are minimized and proper positioning of the catheter is expeditiously accomplished for rapid medical administration. Moreover, the integrated catheter assembly obviates the need for the additional steps of dilating the incision with a dilator(s) in that the catheter of the present invention is self-dilating. According to one aspect of the invention, use of stylets in multi-lumen catheters are selectively used to enhance the rigidity of the assembly and its ability to self-dilate. The integrated catheter of the present invention provides a pre-assembled guidewire within the needle thereby eliminating the need to thread the guidewire though the needle once vascular access is obtained and threading the catheter over the guidewire.

Numerous benefits are achieved by the integrated catheter assembly according to the present invention including a novel catheter for transversely receiving a needle and guidewire which may be pre-assembled in an integrated catheter assembly. One significant benefit is a marked decrease in the time required to percutaneously position the catheter within in a vessel lumen to achieve endovascular access with the catheter due to the elimination of conventional method steps involving the exchange of individual components according to the Seldinger technique. This allows for rapid insertion of the catheter and, hence, rapid administration of medicines or other substances. The pre-assembled integrated catheter assembly obviates the need to provide the discrete units of: catheter, needle, guidewire and a dilator. This eliminates the step of inserting the needle, threading the guidewire within the needle, and positioning the catheter along the guidewire. There is also a decreased risk of the loss of venous access which may occur with prior art methods of exchanging multiple components. The integrated catheter assembly of the present invention also obturates the catheter lumens and prevents complications of air embolism and limits blood loss. The additional needle side port of the catheter, once vacated by the needle and guidewire, beneficially provides an additional port for more rapid administration of greater amounts of medicines or other fluids and provides an additional administration port should the distal port become occluded. The integrated catheter assembly also does not require a separate dilator as the configuration of the various components presents a self-dilating integrated catheter assembly. By decreasing the number of method steps necessary for effective catheter insertion and by eliminating multiple assembly component exchanges over the guidewire, the catheter assembly and method according to the present invention beneficially reduces the risk of catheter related infection; thereby resulting in improved medical outcomes. These and other objectives are met by the present invention.

DETAILED DESCRIPTION OF THE INVENTION

The present invention will now be described in detail hereinafter by reference to the accompanying drawings. The invention is not intended to be limited to the embodiments described; rather, this detailed description is provided to enable any person skilled in the art to make and practice the invention.

Figure 1:
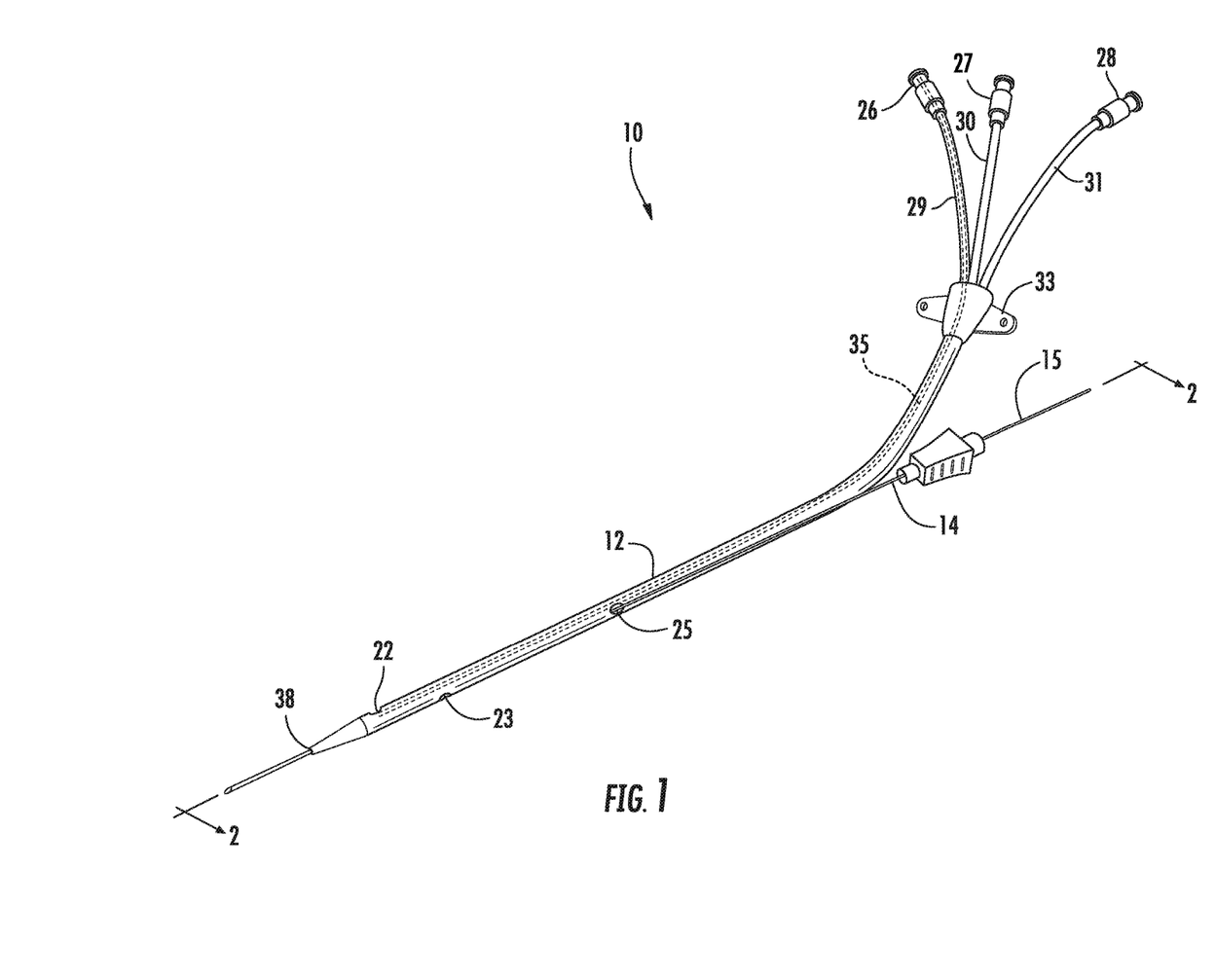
FIG. 1 is a perspective view of the integrated catheter according to the present invention.

The venous catheter assembly 10, as shown in FIG. 1, is used for surgical procedures in which a catheter is inserted percutaneously into the blood vessel for treatment. This treatment may include, for example, the administration of medicine or other fluids, blood pressure monitoring, and/or blood sampling. This invention is not limited, to these uses, as it is within the scope of the present invention to provide a catheter for intravascular access, including, but not limited to, a central, midline or peripheral venous catheter. As is known in the art, the venous catheter as described herein may be used with any cavitary or luminal structure, including any vein. For the sake of discussion, the detailed description herein addresses use of the catheter assembly with any vein. As used herein, the terms "proximal" and "distal" are used to refer to the axial ends of the catheter assembly and various components. The term "proximal end" refers to the end closely adjacent the user of the assembly and the term "distal end" refers to the end of the catheter assembly that is percutaneously inserted into the patient, i.e., adjacent the needle tip. According to the invention illustrated in the various Figures, excluding horizontal cross-sections, the proximal end is toward the right and the distal end is toward the left. Also as used herein, the "axial direction" refers to the longitudinal axis of the catheter from the proximal end to the distal end. The term "transverse" direction refers to a direction which intersects the longitudinal axis, at any angle.

Figure 2:
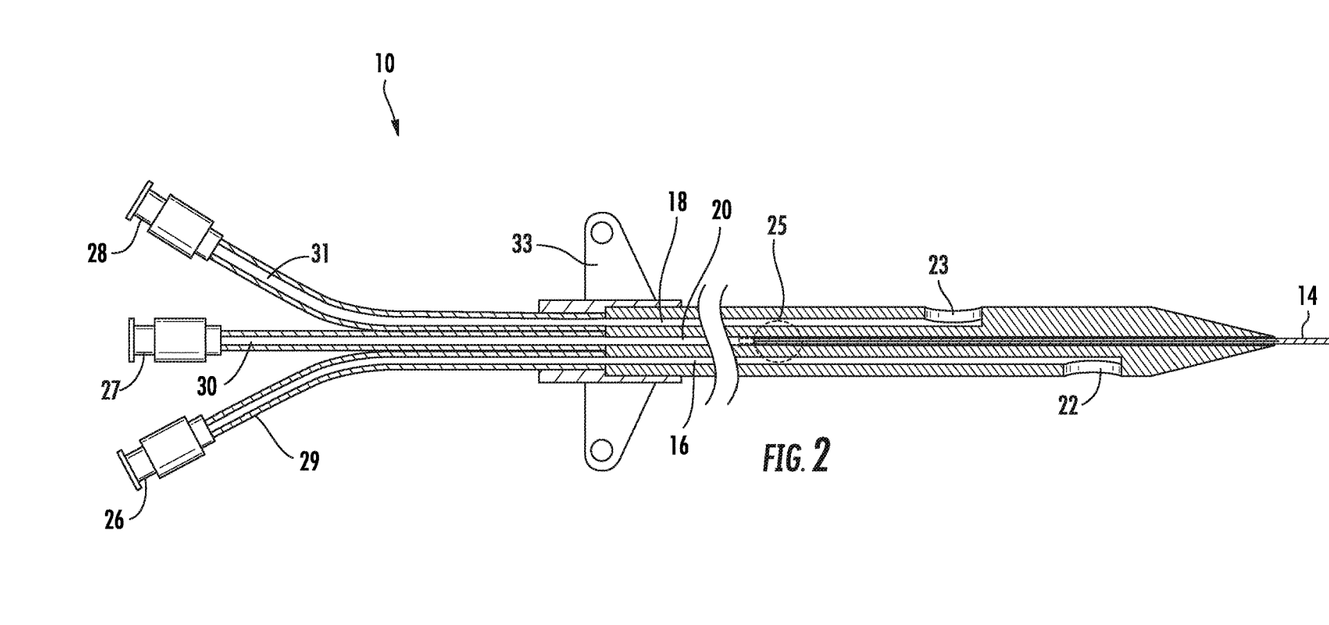
FIG. 2 is a cross-sectional view taken along line 2-2 of FIG. 1.
Figures 3, 4A, 4B, 4C:
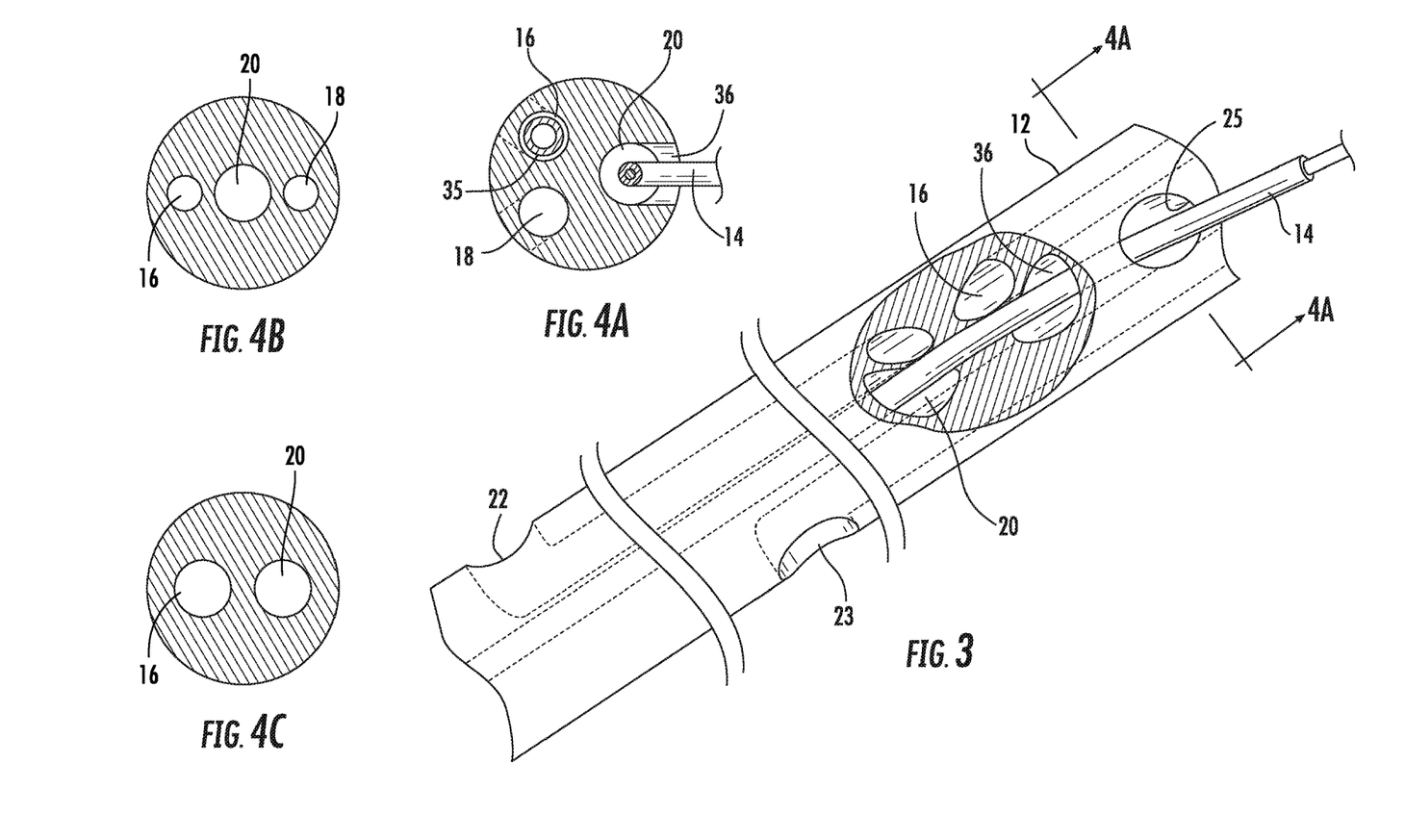
FIG. 3 is an enlarged, partially broken away, view of a needle side port according to the present invention.
FIG. 4A is a cross sectional view of the catheter taken along line 4A in FIG. 3.
FIG. 4B is a cross sectional view according to an alternative aspect of the present invention.
FIG. 4C is a cross sectional view according to another alternative aspect of the present invention.

The venous catheter assembly 10 includes, generally, a novel catheter 12, a needle 14, and a guidewire 15. The catheter assembly 10 illustrated includes three lumens 16, 18, and 20, shown in FIG. 2. Each lumen provides a passageway for the ingress of fluids to or the egress of blood from the vascular system. Although venous catheters may have only a single lumen, such as lumen 20 which extends longitudinally from the proximal end adjacent the user to the distal end for venous insertion, it is more common to provide more than one lumen. Two or three (or more) lumen catheters are commonly utilized for diverse uses of a venous line. Multiple lumens also provide alternative administration or aspiration lumens should more than one lumen be used simultaneously or should one of the other lumens become occluded. The present invention relates to such single or multiple lumen catheters and a catheter assembly including the catheter. FIG. 4 illustrates a triple lumen catheter 12 as described herein in connection with the various other Figures. FIG. 4A, taken along line 4A-4A in FIG. 3, illustrates the cross-sectional view of the catheter assembly 10 according to one aspect of the present invention. FIG. 4A also illustrates a stylet 35 in one lumen, 16, which may selectively be positioned in any of the lumens. (It is noted that FIG. 3 does not include the stylet 35.) FIGS. 4B and 4C illustrate alternative aspects of the present invention. FIG. 4B illustrates a triple lumen catheter 12 including lumens 16, 18 and 20 which are differently positioned within the catheter 12. This is exemplary of various lumen positions contemplated by the present invention. FIG. 4C illustrates a double lumen catheter including the needle lumen 20 and one additional non-needle lumen 16. According to any of these aspects, a stylet 35 may be inserted into one or more of the lumens. Moreover, any known method of providing increased column strength may be utilized without departing from the spirit and scope of the present invention. This includes providing strengthening materials such as heads, coils or wires into the "dead space" (spaced within the catheter exterior to any of the lumens). According to the present invention, it may be desirable to include the stylet 35 into either or all of the non-needle receiving lumens, 16 and/or 18, which extends beyond the lumen side port 22 and/or 23.

The lumen 20 extends the length of the catheter and is configured to receive the needle 14. The one or more additional lumens, 16 and 18 as shown, are referred to as "non-needle lumens". The non-needle lumens 16 and 18 each terminate at a respective side port 22, 23, defined by the catheter outer wall. According to the present invention, a needle side port 25 is also provided as will be described in greater detail below. The side ports 22, 23 of the non-needle lumens 16, 18 establishes intravenous communication of the catheter lumens 16, 18. As such, medicine and/or fluids may be introduced into the catheter, pass through the lumens, and exit the side ports to the vessel in which the catheter has been placed.

Preferably, side ports 22, 23 and 25 are longitudinally separated along the length of the catheter 12. As shown, the needle port 25 is positioned proximal to the non-needle ports 22, 23. This is exemplary, and it is within the scope of the present invention for the needle port to be distally positioned relative to one or more of the other side ports. The distance between the ports 22, 23, 25 is selected in proportion to the catheter's French size so as to axially separate distribution ports wherein multiple fluids may be substantially simultaneously administered through the various lumens. Additionally, the side ports are preferably oriented in a spiral or helical configuration along the catheter body to further separate distribution ports and to sustain the structural integrity of the catheter, particularly during insertion thereof. This configuration also is preferable to avoid multiple ports from becoming simultaneously occluded such as contact with a vessel wall or other intravascular structure. It is envisioned, however, that the various ports may be positioned along that same general side of the catheter and linearly as well.

The venous catheter assembly 10 of the illustrated embodiment is a triple lumen catheter. It is within the scope of the present invention, however, to provide a single lumen 20 and one or more additional non-needle lumens. As shown in FIG. 2, the lumen 20 extends from the proximal end to the distal end of the catheter 12 body. Two additional lumens 16, 18 are shown and each lumen is independent and not communicative with the other lumens 16, 18, 20. The catheter 12 further includes, in the illustrated embodiment, entry ports 26, 27, and 28 which communicate with a respective lumen 16, 18, 20 for the administration of or extraction of fluids or blood. As is known in the art, entry ports 26, 27, 28 may be manipulated to selectively occlude communication of the exterior environment with the lumens. Extension tubes 29, 30, 31 connect the entry ports to a respective lumen and may be of any desired length. Side clamps, not shown, may also be provided along the extension tubes as is known in the art to control the fluid flow through the lumen. As to one aspect of the present invention, a hub 33 joins distal ends of the extension tubes 29, 30, 31 to the proximal end of the catheter 12 to establish communication between the extension tubes and the respective lumen. The hub 33 is provided with a pair of radially extending wings which are advantageously used to further secure the catheter in place with sutures or adhesive-type devices applied to the skin (such as StatLock®).

A stylet 35 in the form of flexible or semi-rigid material, as shown, is provided within one or both non-needle lumens 16, 18 according to an alternative aspect of the present invention. The stylet 35 may likewise be positioned with the needle-receiving lumen 20. Such materials that may be utilized for the stylet include, but are not limited to, solid, hollow, or wire-like plastic or other polymeric material or metal or other alloy (for example, in a tubular configuration). As shown in FIGS. 1 and 4A, lumen 16 comprises a stylet 35 which is selectively inserted into the lumen 16 to improve rigidity in the form of column strength to the catheter. The amount of column strength required and, hence the number and kind of stylet(s), may vary from patient to patient and procedure to procedure. As shown, the stylet 35 extends substantially the axial length of the catheter 12, but it is within the scope of the present invention to provide a stylet within only a portion of the lumen 16. The stylet 35 provides structural rigidity to the catheter 12 which is important as the catheter 12 is percutaneously advanced through the skin, subcutaneous tissues, and blood vessel wall. This is referred to as the catheters "pushability", or ability to possess sufficient rigidity so as to be percutaneously inserted and yet not too rigid so as to cause injury to the vein or surrounding perivascular structures. Moreover, the catheter 12 must remain substantially flexible and pliable for insertion into the venous system. While not being bound by any particular theory, it is believed that the stylet as shown, in combination with the catheter 12 construction, provides sufficient column strength to the catheter 12 for its application while also providing sufficient flexibility for introduction of the catheter into the venous system of a patient. The stylet is to be removed once the catheter is secured in place.

The catheter body 12 defines a novel side port 25 which, as shown, is positioned along the length of the catheter at a position proximal to the non-needle lumen side ports 22, 23. A transverse channel 36 extends from the side port 25 to the lumen 20 to provide open communication there between. As shown in FIG. 3, the transverse channel 36 is angularly positioned relative to the lumen axis and extends transversely with respect thereto. More specifically, the transverse channel 36 as shown extends at an acute angle relative the lumen axis. It is preferred that the angular orientation of the transverse channel 36 be at least approximately 90 degrees or less due to the envisioned angle of needle insertion. The side port 25 is sized, configured and positioned to receive the needle 14.

The catheter assembly 10 may be advantageously provided to include the catheter 12 with a pre-assembled needle 14 and guidewire 15 inserted within the side port 25. As such, the needle 14 extends within a distal portion of the lumen 20 and out the distal tip 38 of the catheter 12. Accordingly, a proximal portion of the needle 14 is contiguous with an outer proximal portion of the catheter, transverse to the lumen axis, while a distal portion of the needle 14 extends co-axially within the lumen 20.

Figure 9:
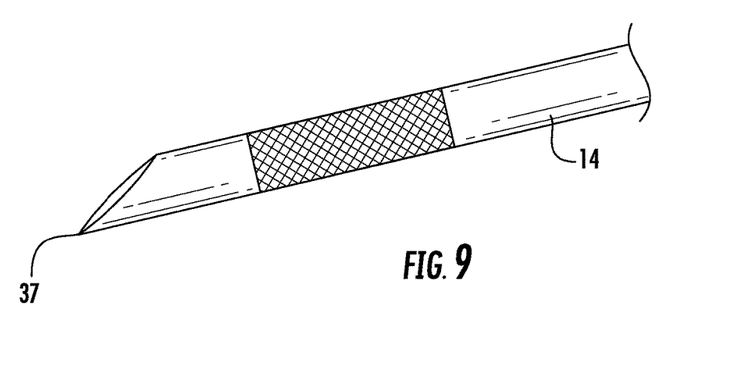
FIG. 9 is an enlarged perspective view of the needle tip.

As shown in FIG. 9, the needle 14 has an insertion tip 37 which is preferably beveled. The gradual taper of the bevel facilitates dilation through the soft tissues and vessel wall for the needle 14 and simultaneously dilates the soft tissues and vessel wall for the catheter 12 insertion. The needle 14 is hollow and may be formed of a surgical grade stainless steel, such as an 18-22 gauge, as is common in the art. As shown in the various Figures, the needle 14 is inserted (preferably prior to use) into the needle side port 25, extends along the length of the transverse channel 36 and enters the lumen 20. The needle 14 extends through a distal aperture on the distal tip 38 of the catheter 12. The distal aperture is preferably sized in accordance with the needle gauge wherein only minimal tolerances are provided for smooth trackability. Preferably, the needle 14 includes an etched portion in the form of a band to provide improved visualization when using ultrasound guidance.

Figure 10:
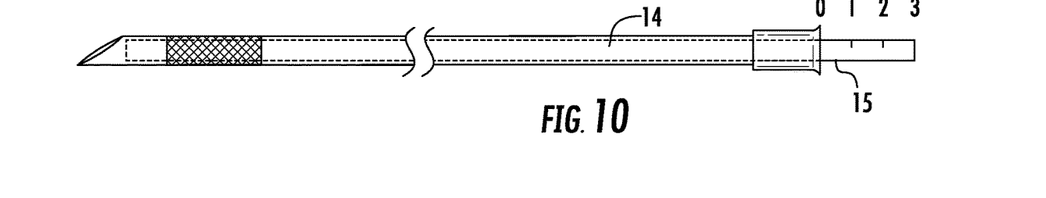
FIG. 10 is a perspective view, partially broken away, of the needle and guidewire.

As shown in FIG. 10, the guidewire 15 extends along the length of the hollow needle 14. The proximal end of the guidewire preferably includes visible marks at regular intervals, for example, 1 cm, to indicate the depth of the wire. This avoids placement too deep within the vasculature, but of sufficient depth for catheter placement. The guidewire 15 may be formed of material known in the art, such as surgical grade wire such as a composite with a nitinol core to provide a blend of stiffness and flexibility, for effective torque control and venous navigation.

Figure 11:
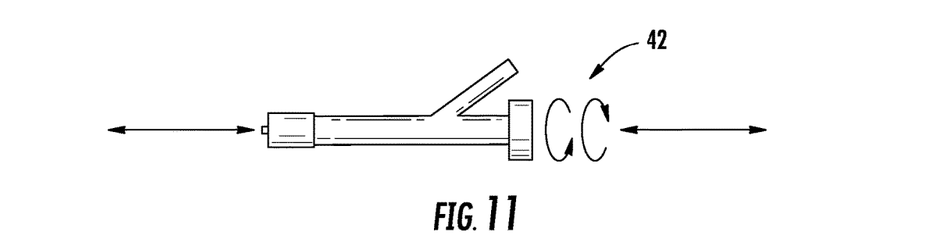
FIG. 11 is a hemostatic valve according to another aspect of the present invention.

FIG. 11 depicts a hemostatic valve 42 which may optionally be used as part of the integrated catheter assembly to facilitate aspiration of the side port 25 to confirm intravascular placement of the catheter 12. The hemostatic valve 42 may be particularly beneficial if ultrasound guided placement is not utilized. The hemostatic valve 42 may be fastened to the proximal hub 33 in a known manner and positioned over the guidewire.

The catheter 12 is a disposable, single use device that is made of a biocompatible material. The stylet, needle, and guidewire may be made of known materials, such as steel, nitinol, or a composition including one or both of these. As set forth above, the stylet 35 may be formed of a plastic or other polymeric or metallic material. The guidewire 15, according to one aspect, is formed of a flexible material to accommodate anatomical complications such as complex and tortuous vasculature. Commonly used materials are a polymeric coated or metallic wire.

Figure 5:
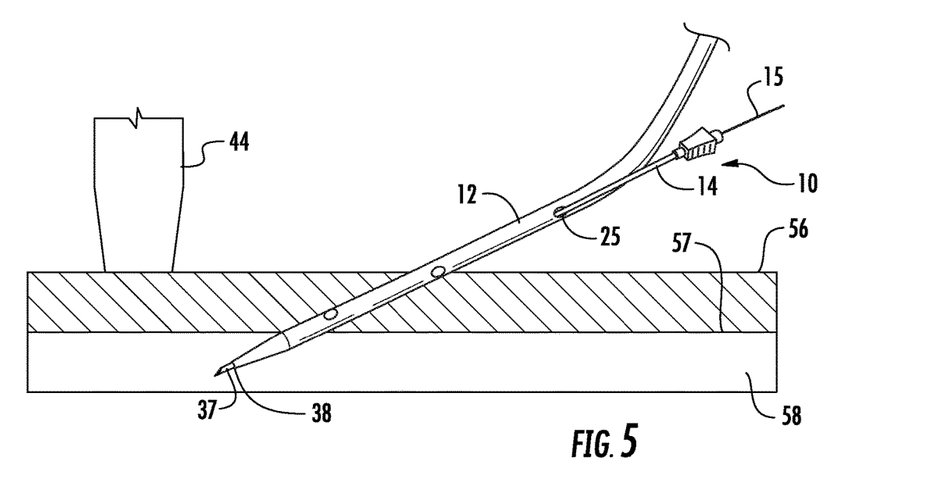
FIG. 5 is a schematic illustration of a method step of inserting the integrated catheter.
Figure 6:
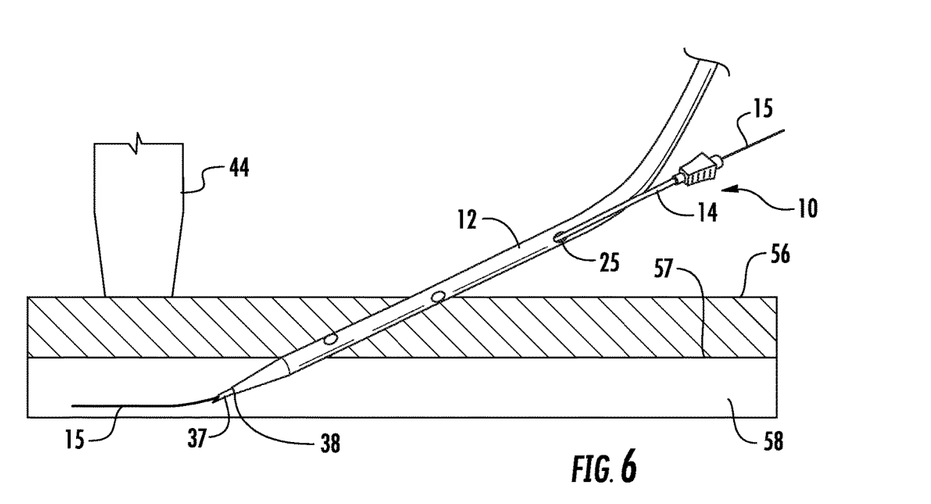
FIG. 6 is a schematic illustration of a subsequent method step of endovascular deployment of the guidewire into the vessel lumen.
Figure 7:
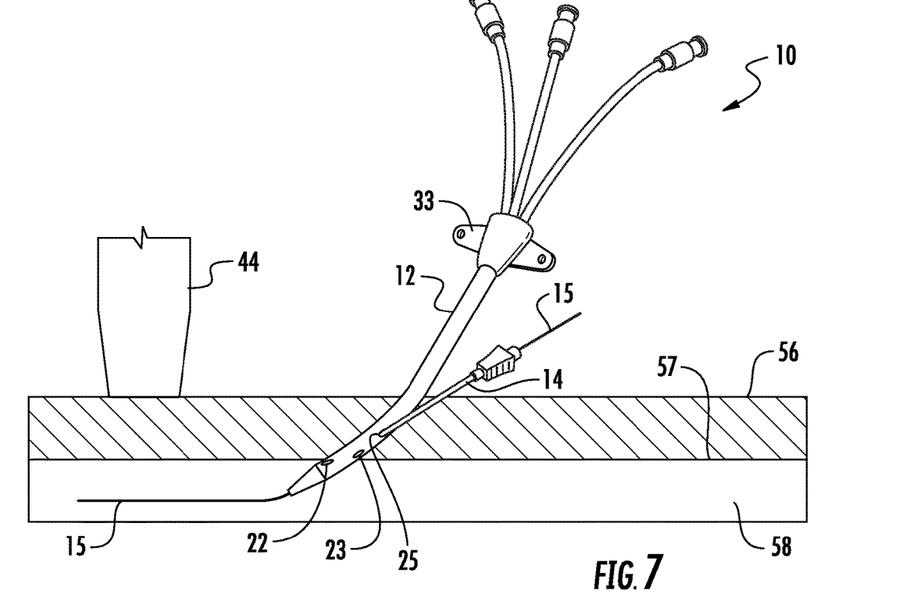
FIG. 7 is a schematic illustration of a subsequent method step of endovascular insertion of the catheter over the needle and guidewire.

FIGS. 5-8 are schematic illustrations of the method of utilizing the integrated catheter for rapid insertion. The integrated catheter assembly 10 is provided with the guidewire 15 positioned within the hollow needle 14 and the needle 14 is positioned within the side port 25. A proximal portion of the needle extends contiguous to and external of a proximal portion of the catheter 12. The distal portion of the needle 14 extends within and along the length of the transverse channel 36 and within and along the length of a distal portion of the lumen 20. The needle insertion tip 37 extends through the distal aperture of the catheter distal tip 38. As shown in FIG. 5, the needle insertion tip 37, preferably utilizing ultrasound guidance 44, penetrates the skin 56, subcutaneous tissue, and the vessel wall 57, entering the target vessel 58. As shown in FIG. 6, once penetration into the vessel is confirmed, by ultrasound or aspiration, endovascular deployment of the guidewire 15 is achieved. The physician advances the guidewire 15 by applying inward force on the proximal end of the guidewire 15, utilizing the visible markings thereon to determine depth of insertion. The physician, while fixing the needle 14 and wire 15 in place, advances the catheter over the needle and wire by applying downward pressure until the catheter 12, too, achieves intravascular placement as shown in FIG. 7.

Figure 8:
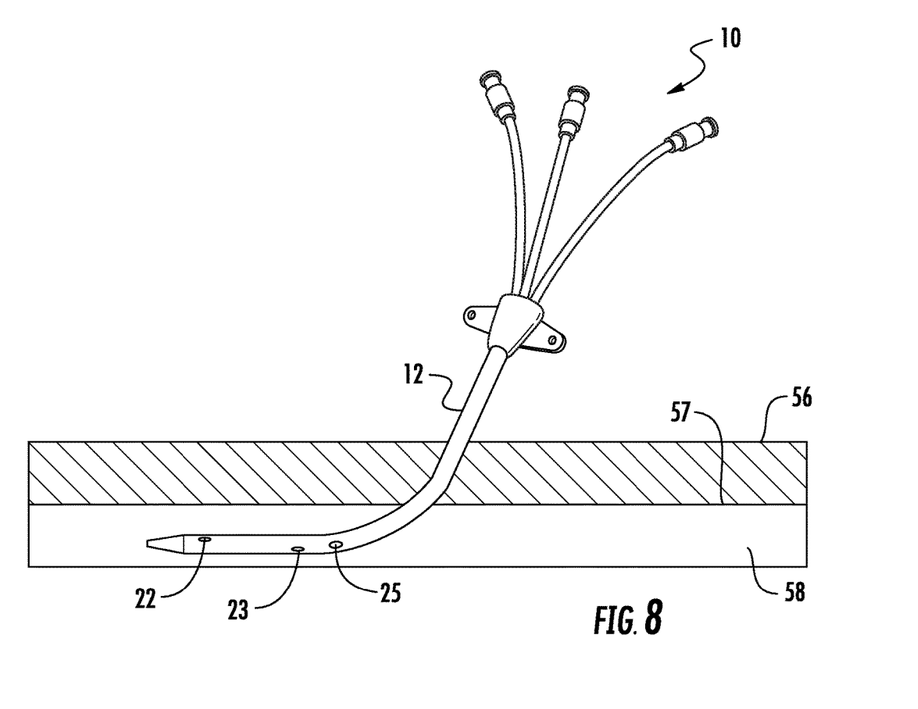
FIG. 8 is a schematic illustration of a subsequent method step of removal of the needle and guidewire from the vessel lumen and the catheter needle side port.

As shown in FIG. 8, the needle 14 and the guidewire 15 are then withdrawn. According to another aspect of the present invention, the needle 14 and guidewire 15 may be removed together, in a single step. The guidewire 15 is then withdrawn and the catheter 12 has been rapidly inserted into the endovascular system. Particularly with the use of ultrasound guidance, this method enables the catheter assembly 10 and, hence, the catheter 12, to be properly and rapidly positioned within the vasculature, without requiring multiple steps of exchanging components as in prior art methods. Moreover, the integrity of the sterile environment is maintained by virtue of utilizing fewer independent components requiring additional and independent manipulation. While not being bound by any particular theory, it is believed that the speed of infusion through the lumen is increased due to the ability of fluids to enter the vasculature from two ports: one at the distal tip 38 and one at the side port 25. It is also believed that because the effective length of the catheter lumen is decreased, at least in part due to Poiseuille's law or other principles, the flow rate is further increased. The integrated catheter assembly 10 decreases the risk of loss of venous access which may occur in prior art methods as components are exchanged. Additionally, the integrated catheter, with one or more stylets, obturates all lumens and prevents complications of air embolism and limits blood loss during insertion.

Alternative embodiments of the present invention include use of specialized antithrombogenic or antibacterial surface coatings, or composites including these, for various components of the catheter assembly. The number of lumens may vary, based upon the intended clinical use. The novel method and catheter assembly according to the present invention may be employed for other vascular access devices and procedures, including, but not limited to, temporary dialysis catheters, peripherally inserted catheters, venous and arterial sheaths, and other vascular access lines or midline catheters. Moreover, the size of various components may be varied for diverse reasons, including, the age of patient, access site, and/or anatomy. A plurality of sizes and lengths may, therefore, be provided. The catheter may be formed of materials having varying stiffness. Conventional catheters are made of a 49 durometer material on the Shore D scale, although other materials or compositions having varying stiffness may be selected, depending upon the clinical need. As described herein, the catheter assembly according to the present invention preferably is positioned utilizing ultrasound guidance. Other guidance techniques, such as fluoroscopy and computed tomography may also be employed. Other guidance techniques, such as palpation, direct visualization, or anatomical landmarks, may also be used to position the catheter assembly according to the present invention.

While exemplary embodiments have been shown and described above for the purpose of disclosure, modifications to the disclosed embodiments may occur to those skilled in the art. The disclosure, therefore, is not limited to the above precise embodiments and that changes may be made without departing from its spirit and scope.

What is claimed is:

1. A catheter assembly for rapid insertion into a vessel comprising:
    a needle having proximal and distal ends, said distal end defining a sharpslistal tip for subcutaneous and vessel insertion, and a longitudinally extending guidewire receiving channel;
    a guidewire having proximal and distal ends positioned within said guidewire receiving channel and extending substantially along a longitudinal length of said needle between said needle ends, said guidewire having a length greater than said longitudinal length of said needle so as to extend distally beyond the distal tip of said needle;
    a catheter having proximal and distal ends and a first longitudinal length defined between said catheter proximal and distal ends and a longitudinally extending first lumen extending between said catheter proximal and distal ends and configured to receive said needle, wherein a distal end of said first lumen defines a distal port for providing intravenous communication, and wherein said first lumen includes a transverse side port in fluid communication with said first lumen when said transverse side port is devoid of said needle, said first lumen transverse side port being defined by an outer side surface of said catheter wherein said first lumen distal port and said transverse side port provide intravenous communication with said first lumen wherein said needle removably extends through said transverse side port and along a portion of said first lumen.

2. The catheter assembly according to claim 1 wherein said side port is positioned along said catheter outer surface at an intermediate location between said catheter proximal and distal ends.

3. The catheter assembly according to claim 2 wherein said catheter further includes a transverse channel which extends from said side port to said first lumen, said transverse channel extending transverse to said first lumen.

4. The catheter assembly according to claim 3 wherein said transverse channel extends at an acute angle relative to a longitudinal axis of said lumen.

5. The catheter assembly according to claim 1 wherein a proximal end of said first lumen defines a proximal port for providing administrative access to said first lumen.

6. The catheter assembly according to claim 2 comprising a second longitudinally extending lumen which extends from said catheter proximal end to a second lumen side port defined by an outer surface of said catheter for providing fluid communication with said second lumen for fluid administration wherein said first and second lumens are substantially not in fluid communication.

7. The catheter assembly according to claim 6 wherein said second lumen side port is positioned along said catheter outer surface at a distance distal to said first lumen side port.

8. The catheter assembly according to claim 6 comprising a third longitudinally extending lumen which extends from said catheter proximal end to a third lumen side port, said third lumen side port being defined by an outer surface of said catheter for providing open communication with said third lumen side port for fluid administration wherein said third lumen is positioned along said catheter outer surface at a distance distal to said first lumen side port.

9. The catheter assembly according to claim 8 wherein said second and third lumen side ports and said transverse side port are positioned in a helical configuration around said catheter outer surface.

10. The catheter assembly according to claim 1 further comprising a reinforcing member for providing column strength to said catheter.

11. A catheter assembly for rapid insertion into a vessel comprising:
    a needle having proximal and distal ends, the distal end defining a sharp distal tip for subcutaneous and vessel insertion, and a longitudinally extending guidewire receiving channel;
    a guidewire having proximal and distal ends positioned within said guidewire receiving channel and extending substantially along a longitudinal length of said needle at least between said needle ends and having a length greater than said needle longitudinal length so as to extend distally beyond the distal tip of said needle;
    a catheter having proximal and distal ends and a first longitudinal length defined between said catheter proximal and distal ends and a longitudinally extending first lumen extending between said catheter proximal and distal ends and configured to receive said needle, wherein a distal end of said first lumen defines a distal port for providing intravenous communication, a lumen proximal end defines a proximal port, wherein said needle extends within said first lumen a second longitudinal length defined from said distal end of said catheter to an intermediate location along said catheter length, said needle second longitudinal length being less than said catheter first longitudinal length and a proximal portion of said needle extends external of and adjacent to an outer portion of said catheter transverse to said first lumen wherein said first lumen is in fluid communication with a side port configured at said intermediate location when said side port is devoid of said needle for administration of fluids from said side port.

12. The catheter assembly according to claim 11 wherein said catheter further includes a transverse channel which extends from said side port to said first lumen, said transverse channel extending transverse to said first lumen wherein said first lumen is in fluid communication with said distal port and transverse side port at said intermediate location for administration of fluids.

13. The catheter assembly according to claim 12 wherein said transverse channel extends at an acute angle relative to a longitudinal axis of said lumen.

14. The catheter assembly according to claim 10 wherein said reinforcing member is removable and is positioned within said first lumen in a proximal portion thereof which is not occupied by said needle.

15. The catheter assembly according to claim 1 wherein said side port is configured for fluid administration.

16. The catheter assembly according to claim 1 wherein said side port is positioned along said catheter length to achieve vascular access for fluid administration.

17. The catheter assembly according to claim 11 wherein said side port is configured for fluid administration.

18. The catheter assembly according to claim 11 wherein said side port is positioned along said catheter length to achieve vascular access for fluid administration.

* * * * *

UNITED STATES PATENT AND TRADEMARK OFFICE
CERTIFICATE OF CORRECTION

PATENT NO. : 10,376,675 B2
APPLICATION NO. : 15/008628
DATED : August 13, 2019
INVENTOR(S) : James D. Mitchell and Andrew A. Thoreson It is certified that error appears in the above-identified patent and that said Letters Patent is hereby corrected as shown below:

In the Claims

Column 9, Line 44: Replace "sharpslistal" with --sharp distal--.

Signed and Sealed this
Sixteenth Day of August, 2022

*Katherine Kelly Vidal*

Katherine Kelly Vidal
*Director of the United States Patent and Trademark Office*